United States Patent [19]

Bustillo

[11] Patent Number: 5,005,583

[45] Date of Patent: Apr. 9, 1991

[54] DIAGNOSTICS PROCEDURES IN UNEXPLAINED FEMALE INFERTILITY

[75] Inventor: Maria del Carmen Bustillo, Cabin John, Md.

[73] Assignee: Research & Education Institute, Inc. Harbor-UCLA Medical Center, Torrance, Calif.

[21] Appl. No.: 76,353

[22] Filed: Jul. 22, 1987

[51] Int. Cl.$^5$ .............................................. A61B 10/00
[52] U.S. Cl. ...................................... 128/738; 604/55
[58] Field of Search ................................ 128/749–750, 128/738; 604/49, 54–55

[56] References Cited

U.S. PATENT DOCUMENTS

| 3,811,443 | 5/1974 | Dickinson, III et al. | 604/55 |
| 3,815,580 | 6/1974 | Oster | 604/55 X |
| 4,036,212 | 7/1977 | Karuhn | 128/738 |
| 4,232,673 | 11/1980 | Bucalo | 604/55 X |
| 4,563,172 | 1/1986 | Ferguson | 604/55 |
| 4,589,402 | 5/1986 | Hodgen et al. | 604/55 X |
| 4,628,940 | 12/1986 | Naslund | 128/750 |
| 4,642,094 | 2/1987 | North, Jr. et al. | 604/55 |
| 4,670,401 | 6/1987 | Cutler et al. | 128/738 X |
| 4,675,286 | 6/1987 | Calenoff | 128/749 X |
| 4,701,161 | 10/1987 | Lenck | 604/55 |
| 4,709,705 | 12/1987 | Truglio | 128/750 |

FOREIGN PATENT DOCUMENTS 2070437 9/1981 United Kingdom ................ 604/55

Primary Examiner—Lee S. Cohen
Assistant Examiner—John P. Lacyk
Attorney, Agent, or Firm—Drucker & Sommers

[57] ABSTRACT

A method for the diagnosis and treatment of infertile women, utilizing nonsurgical, transcervical uterine lavage to recover ova for the purpose of analysis, morphologic assessment, and treatment.

13 Claims, No Drawings

DIAGNOSTICS PROCEDURES IN UNEXPLAINED FEMALE INFERTILITY

BACKGROUND OF THE INVENTION

This invention relates to human infertility, in particular the apparent inability of certain women to conceive. There are many currently known causes of infertility, including: abnormality in the male partner, ovulatory disorder, abnormal sperm-cervical mucus interaction, tubal obstructive disease and/or endometriosis, luteal phase defect, and a variety of peritoneal, ovarian and immunologic factors. Many women, however, fail to conceive despite all current diagnostic studies for infertility being normal.

One approach to treatment involves an effort to understand and remedy an infertile woman's own ability to conceive. There have been theories advanced in the art to identify the *causes* of infertility which cannot be explained by the causes set forth above, and a wide variety of etiologic factors are being currently investigated. Current theories include luteinized unruptured follicle syndrome, autoantibodies against the zona pellucida, or failure of implantation of the conceptus. However, none of these theories currently aid the clinician in directing treatment for unexplained infertility, and past therapies have been largely empiric in nature.

Alternative approaches to treatment involve compensating for a women's inability to conceive by way of "substituting" another women's ovum. One method, for example, involves the donation of a fertilized ovum from a fertile woman to an infertile receipient woman. These include in-vitro fertilization, where the oocyte of a donor is surgically removed from the body, fertilized in a laboratory vessel (in-vitro), and then the fertilized ovum is non-surgically placed into the uterus of an infertile recipient woman (Lutjen, P, et al., "The Establishment and Maintenance of Pregnancy Using In Vitro Fertilization and Embryo Donation in a Patient with Primary Ovarian Failure," *Nature*, 307, 174 (1984)). Additionally, nonsurgical ovum transfer is a recently developed treatment for infertile women, involving the nonsurgical recovery of an in vivo fertilized human ovum from a fertile donor, and its nonsurgical transfer to an infertile recipient woman. These techniques are not directed to discerning the cause of the recipient woman's infertility.

An apparatus has been developed which is useful for embryonation and human embryo transfer, and for uterine examination and treatment. U.S. Pat. No. 4,533,345 describes a uterine catheter designed for nonsurgical, transcervical "probing of the uterus, non-surgically recovering pre-implantation embryos, flushing the uterus, testing for tubal patency, introducing a treative material into the uterus, and sampling endometrial or uterine tissue." Particularly, the uterine catheter in that invention is preferably used for non-surgical human embryo recovery in processess for human embryo transfer and artificial embryonation (Column 2, lines 33-43).

U.S. Pat. No. 4,533,345 thus teaches the practice of its invention to recover *fertilized* ova, and for probing and treating uterine and tubal factors.

It is also possible that some infertility may result from characteristics of a woman's ova. However, until recently, it has not been possible, except by surgical means, to recover an ovum, fertilized or unfertilized, or to assess its morphology. Detection of a fertilized ovum likewise has not been possible except by surgical means, or blood serum analysis, until after implantation. Additionally, the only method for determining the viability of any ovum after its recovery from a woman has been the clinical test of replacing it in the woman.

Applicant is aware of experiments performed on mice involving the sacrificing of the mice, and then the surgical removal and examination of fertilized and unfertilized ova.

There has long been a need for a method of precise, nonsurgical diagnosis and treatment of infertile women whose infertility cannot be explained by current state-of-the-art methods.

SUMMARY

In accordance with this invention, a novel diagnosis and treatment method is provided for apparently infertile women whose infertility cannot be explained by current methods. This new method involves nonsurgical, trascervical uterine lavage of a woman's uterus, and methods for the diagnosis of such unexplained infertility. A further object of this invention is directed to the nonsurgical recovery, analysis, and treatment of unfertilized ova.

DETAILED DESCRIPTION

As described generally above, this invention relates to a method of diagnosis and treatment of apparently normally ovulatory but infertile woman, and more particularly to women whose infertility cannot be explained by the use of standard and contemporary diagnostic methods.

An initial step of the method of this invention involves tracking a woman's ovulatory cycle by known methods (e.g. by measuring blood serum hormone levels), to determine an estimated approximate time of ovulation. It may be desirable to omit the above initial step, and perform the second or third and subsequent steps of the method of this invention.

Secondly, the woman is inseminated with normal human semen, either by intercourse or artificial insemination, at or around the estimated time of ovulation. In an alternative embodiment of the method of this invention, this second step may be omitted.

Next, a transcervical uterine lavage is performed on the woman preferably five days after, but within two to seven days after the insemination (or estimated time of ovulation), or within a period before implantation of a fertilized ovum into the uterus is statistically believed to occur. The lavage fluid is retained. A uterine catheter such as described above in U.S. Pat. No. 4,533,345 is suitable for performing such a lavage. A suitable lavage fluid is sterile physiologic buffered saline with approximately five percent human serum albumin.

The retained lavage fluid is then scanned, microscopically, for the presence or absence of an ovum, fertilized or unfertilized. Preferably, any blastospheres recovered which appear viable by standard criteria are nonsurgically returned to the woman's uterus by a known catheter methodology in a solution of suitable media such as is known in the art as Ham's F-10 with approximately 20 percent human inactivated cord serum.

If an ovum is recovered from a woman who was not inseminated, or if a fertilized or unfertilized ovum is recovered which appears to be non-viable by standard criteria, such ovum is then examined and analyzed. Suitable tests include chromosome checking and ultrastructural examination by transmission electron microscopy.

The practice of this invention requires the analysis of several possible outcomes to the above steps to identify specific causes of the infertility so that appropriate treatments may be devised. By way of illustration, below are examples of the analytical method which is a part of this invention.

If, for example, lavage repeatedly fails to recover an ovum, this may be due to nonrupture of the follicle (which is known as ovulation failure and is currently only susceptible to a presumed ultrasound diagnosis or identification by surgically taking a slice of an ovary for examination), or to a failure of tubal transport.

In these instances, treatment could, for example, either be embryonation with an ovum from a donor woman, or treatment designed to effectively eliminate any tubal blockage or defects in the internal tubular architecture.

If, for example, an ovum is recovered, it can be undivided or divided. If the ovum is undivided, electron microscopy can show if sperm did or did not enter. If an ovum is undivided and there is no sperm present (e.g. demonstrated by an absence of sperm fragments upon ultra-structural examination), treatment could involve using different (or donated) ova. If an ovum is undivided and no sperm is present, substituting either different ova or different sperm could be an appropriate treatment. There are a variety of factors involved in the penetration of ova by sperm, which may be further examined if desired.

If ova are recovered which are divided, the division may be proceeding normally or abnormally. If, for example, normally dividing ova are repeatedly recovered and returned to the woman's uterus and do not lead to a pregnancy, then further examination of the uterine lining could be necessary, or alternatively, treatment could be to transfer a fertilized ovum into a fertile surrogate to carry the conceptus to term.

If an ovum is dividing abnormally, it can be after contact with sperm, or not (parthenogenesis). If, for example, ova are abnormally dividing but repeatedly are penetrated by normal sperm, the treatment could require donation of new ova by a fertile donor woman.

Electron microscopy may be used to ascertain extensive information about cleavage abnormality (e.g. whether cleavage occurred after the pronucleii formed). Alternatively, chromosomes may be checked to determine if there is an abnormal number of chromosomes or if the ova was penetrated by more than one sperm (polyspermy).

A variety of standard diagnostic procedures may be contemporaneously employed, including, for example, sampling of blood serum hormones, or of urine.

Many morphological examinations and many alternative treatments may be utilized for the practice of this invention. The specific embodiments and methods set forth above are merely illustrative, and may be varied or modified, or different tests or treatments could be used to produce the same desirable results without departing from the scope of the inventive concept.

I claim:

1. A method for the diagnosis and treatment of an infertile woman having a normal ovulatory cycle, comprising the steps of:
    (a) tracking said woman's ovulatory cycle to determine estimated approximate time of ovulation;
    (b) inseminating said woman with normal human semen at or around said estimated approximate time of ovulation;
    (c) performing a nonsurgical transcervical uterine fluid lavage on said woman within two to seven days after said insemination and recovering and retaining the lavage fluid;
    (d) scanning said retained lavage fluid for the presence of an ovum; and
    (e) examining any ovum present within said retained lavage fluid for the purpose of rendering a diagnosis and treatment.

2. The method of claim 1, wherein said ovulatory cycle tracking is accomplished by measuring said woman's serum hormone levels.

3. The method of claim 1, wherein said ovulatory cycle tracking is accomplished by examining said woman's endometrial configuration.

4. The method of claim 1, wherein said fluid lavage utilizes sterile physiological buffered saline and human serum albumin.

5. The method of claim 1, wherein said nonsurgical transcervical uterine lavage is performed approximately five days after said insemination.

6. The method of claim 1, wherein an ovum is recovered, examined, and reintroduced into the uterus of said woman.

7. The method of claim 1, wherein an ovum is recovered, and subjected to diagnostic tests.

8. The method of claim 7, wherein said diagnostic test comprises an ultrastructural examination of said ovum.

9. The method of claim 7, wherein said diagnostic test comprises examination by electron microscopy.

10. The method of claim 7, wherein said diagnostic test comprises chromosomal examination.

11. The method of claim 7, wherein a treatment for said woman is developed which responds to said diagnostic tests.

12. A method for the diagnosis and treatment of an infertile woman having a normal ovulatory cycle, comprising the steps of:
    (a) inseminating said woman with normal human semen at a chosen time;
    (b) performing a nonsurgical transcervical uterine fluid lavage on said woman within two to seven days after said insemination and recovering and retaining the lavage fluid;
    (c) scanning said retained lavage fluid for the presence of an ovum; and
    (d) examining any ovum present within said retained lavage fluid.

13. A method for the diagnosis and treatment of an infertile woman having a normal ovulatory cycle, comprising the steps of:
    (a) tracking said woman's ovulatory cycle to determine estimated approximate time of ovulation;
    (b) performing a nonsurgical transcervical uterine fluid lavage on said woman within two to seven days after said estimated approximate time of ovulation and recovering and retaining the lavage fluid;
    (c) scanning said retained lavage fluid for the presence of an ovum; and
    (d) examining any ovum present within said retained lavage fluid.

* * * * *